United States Patent
McArthur et al.

(10) Patent No.: US 10,926,076 B2
(45) Date of Patent: Feb. 23, 2021

(54) HEMOSTASIS TORQUE ASSEMBLY

(71) Applicant: Merit Medical Systems, Inc., South Jordan, UT (US)

(72) Inventors: Gregory R. McArthur, Sandy, UT (US); Kenneth Sykes, Bluffdale, UT (US); Richard P. Jenkins, Bluffdale, UT (US); Steve Carlstrom, Salt Lake City, UT (US); Jim Mottola, West Jordan, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 124 days.

(21) Appl. No.: 15/974,117

(22) Filed: May 8, 2018

(65) Prior Publication Data
US 2018/0326197 A1 Nov. 15, 2018

Related U.S. Application Data

(60) Provisional application No. 62/503,627, filed on May 9, 2017.

(51) Int. Cl.
*A61M 39/06* (2006.01)
*A61M 25/09* (2006.01)

(52) U.S. Cl.
CPC .. *A61M 39/0613* (2013.01); *A61M 25/09041* (2013.01); *A61M 2025/09125* (2013.01); *A61M 2039/062* (2013.01); *A61M 2039/0626* (2013.01); *A61M 2039/0673* (2013.01); *A61M 2205/582* (2013.01)

(58) Field of Classification Search
CPC ........ A61M 39/0613; A61M 25/09041; A61M 2039/062; A61M 2025/09125; A61M 2039/0626; A61M 2039/0673; A61M 2205/582; A61M 39/06
See application file for complete search history.

(56) References Cited

U.S. PATENT DOCUMENTS

| | | | |
|---|---|---|---|
| 5,117,839 A | 6/1992 | Dance | |
| 5,836,306 A | 11/1998 | Duane et al. | |
| 6,287,280 B1 * | 9/2001 | Lampropoulos | A61M 39/0693 604/165.01 |
| 2002/0002352 A1 | 3/2002 | Becker et al. | |

(Continued)

FOREIGN PATENT DOCUMENTS

WO 2009131862 10/2009

OTHER PUBLICATIONS

International Search Report and Written Opinion dated Sep. 28, 2018 for PCT/US2018/031606.
European Search Report dated Aug. 19, 2020 for EP18798449.7.

*Primary Examiner* — Theodore J Stigell
*Assistant Examiner* — Daniel Moore
(74) *Attorney, Agent, or Firm* — Stoel Rives LLP

(57) ABSTRACT

The present disclosure relates to a hemostasis valve with a selectively coupled torque device. The hemostasis valve may include a first mating interface, and the torque device may comprise a second mating interface. The first interface may comprise a groove that retains the second interface, which may comprise a ridge. An axial force may couple and decouple the interfaces. The interfaces may be configured to allow the torque device to rotate relative to the hemostasis valve when in a coupled position.

17 Claims, 5 Drawing Sheets

(56) References Cited

U.S. PATENT DOCUMENTS

| | | | |
|---|---|---|---|
| 2004/0210194 A1 | 10/2004 | Bonnette et al. | |
| 2005/0085789 A1* | 4/2005 | Khan | A61M 39/0613 604/500 |
| 2007/0010796 A1 | 1/2007 | Moran et al. | |
| 2009/0259200 A1* | 10/2009 | Lampropoulos | A61M 39/0613 604/249 |
| 2010/0036329 A1 | 2/2010 | Razack | |
| 2013/0253565 A1* | 9/2013 | Myers | A61M 29/02 606/194 |
| 2013/0303330 A1* | 11/2013 | Stevens | A61M 25/09041 475/349 |
| 2016/0175564 A1 | 6/2016 | Eberle | |

* cited by examiner

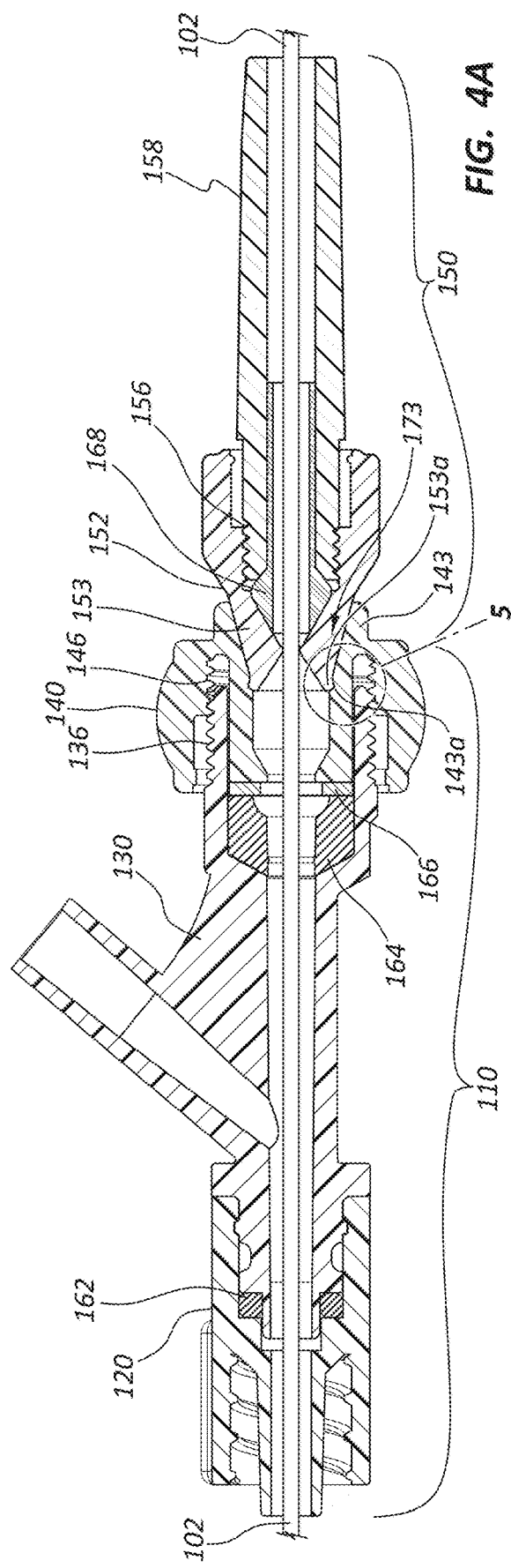
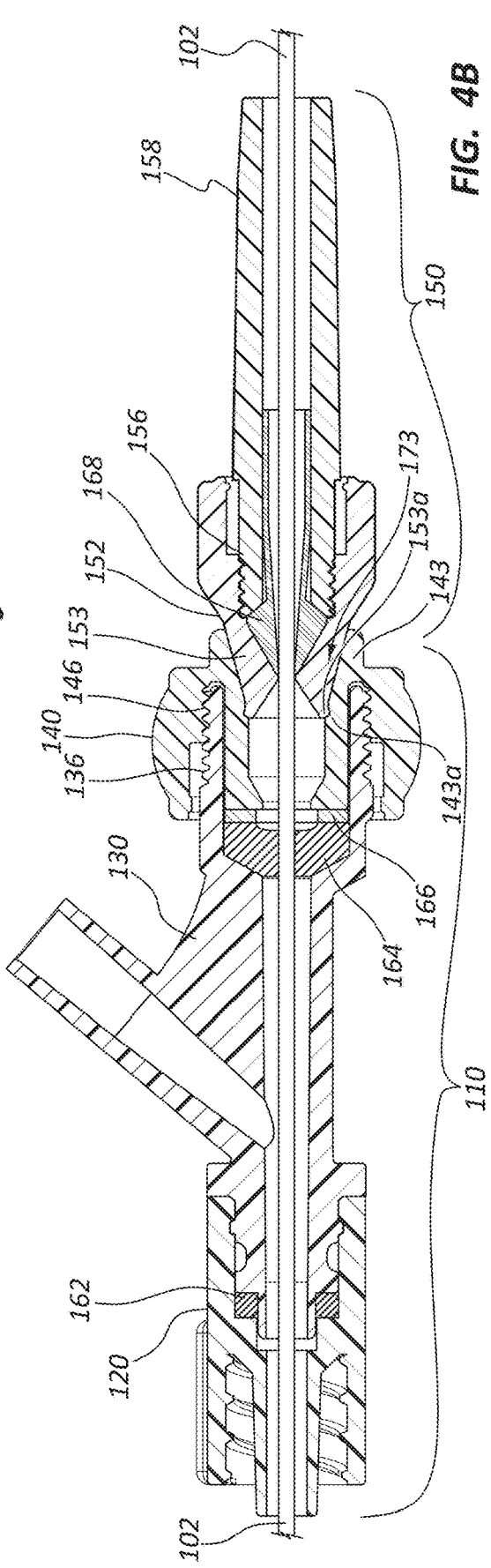

HEMOSTASIS TORQUE ASSEMBLY

RELATED APPLICATIONS

This application claims priority to U.S. Provisional Application No. 62/503,627, filed on May 9, 2017 and titled "Hemostasis Torque Assembly" which is hereby incorporated by reference in its entirety.

TECHNICAL FIELD

The present disclosure relates generally to the field of medical devices. More particularly, embodiments disclosed herein relate to a hemostasis valve with a selectively coupled torque device.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which:

FIG. 4A illustrates a cross-sectional view of the hemostasis torque assembly of FIG. 1 taken through plane 4A-4A in a first position where a guidewire is unsecured, according to one embodiment.

FIG. 4B illustrates a cross-sectional view analogous to the view of FIG. 4A of the hemostasis torque assembly of FIG. 1, in a second position where the guidewire is secured, according to one embodiment.

DETAILED DESCRIPTION

Figure 1:
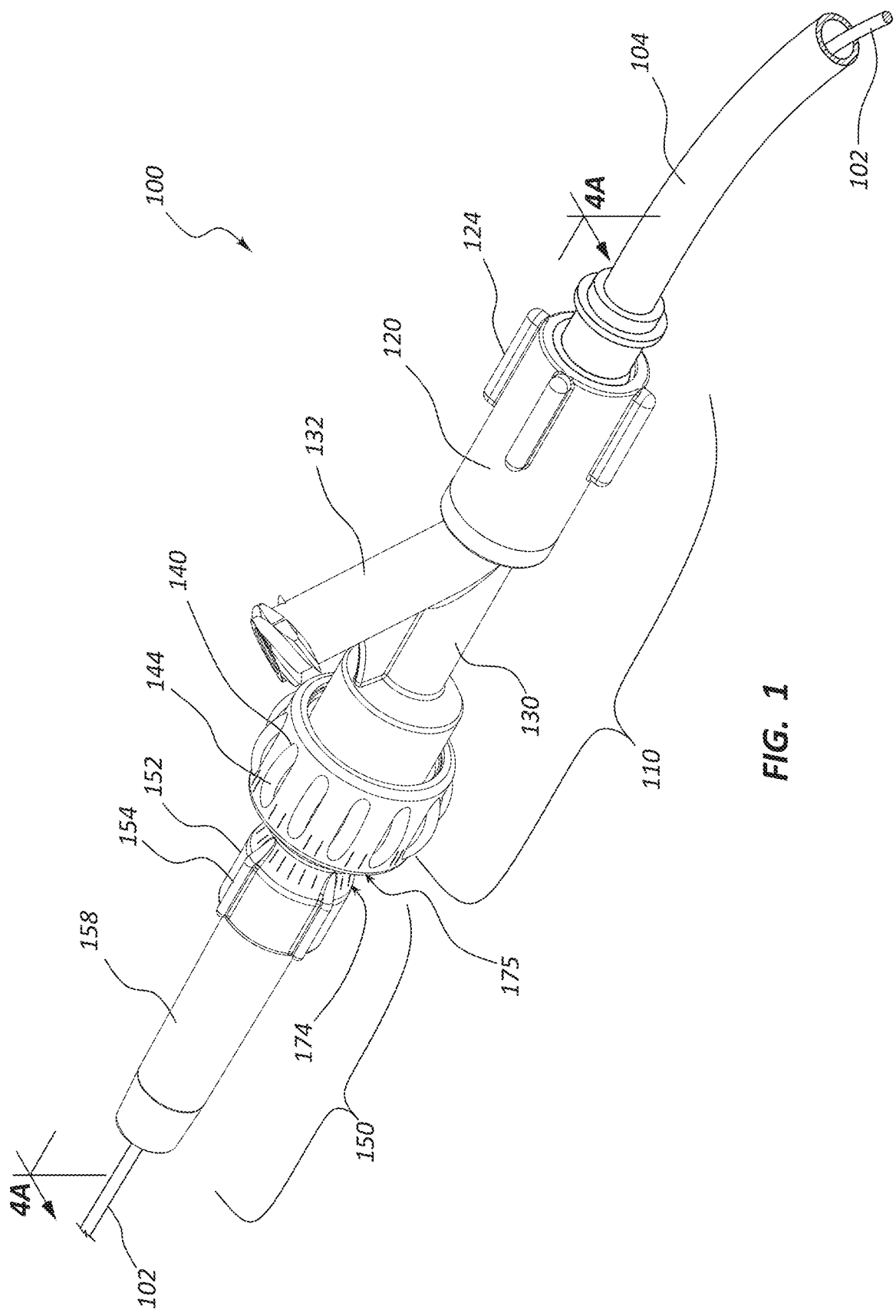
FIG. 1 illustrates a perspective view of a hemostasis torque assembly in a coupled position, according to one embodiment.

This disclosure describes a hemostasis torque assembly that may comprise a hemostasis valve with a snap-fit torque device. In some instances, the hemostasis torque assembly provides access to a cardiovascular system of a patient and control of inserted guidewires. Various medical procedures require temporary and often repeated introduction and removal of catheters and/or guidewires within the cardiovascular system of a patient. These procedures introduce complications such as controlling a patient's bleeding and precisely manipulating an inserted catheter or guidewire.

Additionally, the placement of inserted medical tools facilitates proper treatment. In some procedures, guidewires are designed to navigate blood vessels to reach a target vessel segment. Once at the target vessel segment, the guidewire may act as a guide for catheters or other devices. Thus, the position of a guidewire may further facilitate proper placement of medical devices. In some operations, after a medical device is guided to a treatment site, the guidewire is removed while the medical device is used. A physician may need to later reinsert the guidewire to guide additional medical tools to the treatment site. However, reinsertion of a guidewire may alter the axial displacement and/or rotational angle of the guidewire.

Further, the positional relationship between the end of a guidewire and the end of a catheter may also be related to storage and shipment of a catheter system. For example, to assist with insertion into a blood vessel, a catheter may have a curved end. For shipment, the catheter may be coupled to the hemostasis valve and a guidewire inserted into the catheter. However, if the guidewire extends to the curved end of the catheter, the guidewire may exert a force on the catheter that causes the curved end to lose its form. Thus, in some instances, a guidewire may be placed offset from the curved end during shipping and storage.

A hemostasis valve with a snap-fit torque device (hemostasis torque assembly), as described herein, may facilitate control of rotational and axial displacement of a guidewire while limiting fluid loss. To control patient bleeding, the hemostasis valve may restrict blood flow while facilitating easy insertion and removal of the catheter and/or guidewire within the cardiovascular system. For example, one end of a hollow introducer may be inserted within a blood vessel of a patient. The opposite end of the introducer would be positioned outside the body of the patient and attached to the hemostasis valve. The hemostasis valve may comprise an opening that provides access for medical tools to enter the introducer, and a seal that prevents blood from escaping.

The snap-fit torque device may selectively secure, engage, or grip an elongate medical device and facilitate displacement, such as translation or rotation, of the elongate medical device by manipulation of the torque device. The snap-fit torque device may also selectively couple to the hemostasis valve to limit the movement of a secured medical device. For example, during shipping the snap-fit torque device may couple to the hemostasis valve and fix the positional relationship between the end of a guidewire and the end of a catheter.

The selective coupling of the snap-fit torque device and the hemostasis valve may also assist in reinsertion of a medical device. For example, the snap-fit torque device may be removed from the hemostasis valve along with a secured guidewire, thereby allowing the axial position of the snap-fit torque device on the secured guidewire to be retained. By retaining the position of the snap-fit torque device on the guidewire, the snap-fit torque device facilitates reinsertion of the secured guidewire with limited axial and/or rotational displacement.

In some embodiments described herein, a hemostasis torque assembly may include a body comprising a valve lumen extending from a proximal end to a distal end of the body. A seal with a sealable opening may abut the proximal end of the body. A compression nut may selectively apply pressure to the seal and alter the diameter of the sealable opening. The compression nut may include a first mating mechanism.

The hemostasis torque assembly may further include a torque nut with a second mating mechanism configured to selectively couple to the first mating mechanism. A collet within the torque nut may selectively provide a clamping force to maintain a position of a guidewire extending through the collet. A collet handle may couple to the torque nut and selectively alter the clamping force of the collet based on the axial position of the collet handle relative to the torque nut.

The body may include features to increase functionality of the hemostasis torque assembly. For example, the body may comprise a sidearm to provide an additional path to the valve lumen. In some embodiments, the body may include an interface configured for coupling to intravascular access medical devices, for example a luer interface.

The mating mechanisms may be physical structures that selectively couple the compression nut and the torque nut. For example, the mating mechanisms may be opposing halves of a snap-fit connector. In some embodiments, the first mating mechanism comprises a groove within the compression nut, and the second mating mechanism comprises a ridge on an exterior surface of the torque nut. In some embodiments, the second mating mechanism comprises a flare at a proximal end of the torque nut.

A physician may apply several different directional forces to the hemostasis torque assembly to accomplish various tasks. In some embodiments, the seal opening diameter may be changed by rotating the compression nut, and the clamping force may be adjusted by rotating the torque nut. Additionally, the torque nut and the compression nut may be rotatable relative to each other to alter the rotational angle of the guidewire. In some embodiments, the first and the second mating mechanisms include resistance and/or indexing to provide tactile feedback to a user when the torque nut is rotated.

In some embodiments, to retain the coupling between the compression nut and the torque nut, a different force may be used to couple the nuts than the force used to adjust the seal opening and adjust the clamping force. For example, the first and second mating mechanisms may be coupled via an axial force.

The phrase "coupled to" is broad enough to refer to any suitable coupling or other form of interaction between two or more entities, including mechanical, fluidic, and thermal interaction. Thus, two components may be coupled to each other even though they are not in direct contact with each other. The phrase "attached to" refers to interaction between two or more entities which are in direct contact with each other and/or are separated from each other only by a fastener of any suitable variety (e.g., mounting hardware or an adhesive).

Axial displacement refers to movement in a longitudinal direction of an elongated member. Rotational displacement refers to a change in angle of an elongated member about an longitudinal axis.

The terms "proximal" and "distal" are opposite directional terms. The distal end of a device or component is the end of the component that is furthest from the physician during ordinary use. The proximal end refers to the opposite end, or the end nearest the physician during ordinary use.

The components of the embodiments as generally described and illustrated in the figures herein can be arranged and designed in a wide variety of different configurations. Thus, the following more detailed description of various embodiments, as represented in the figures, is not intended to limit the scope of the present disclosure, but is merely representative of various embodiments. While various aspects of the embodiments are presented in drawings, the drawings are not necessarily drawn to scale unless specifically indicated.

FIG. 1 illustrates a perspective view of a hemostasis torque assembly 100 in a coupled position, according to one embodiment. The hemostasis torque assembly 100 may facilitate manipulation of a guidewire 102 while limiting fluid loss. The hemostasis torque assembly 100 illustrated in FIG. 1 includes a torque element or torque device 150 and a hemostasis valve 110 selectively coupled together.

The torque device 150 is configured to selectively secure, engage, or grip an elongate medical device and facilitate displacement, such as translation or rotation, of the elongate medical device by manipulation of the torque device 150. For example, as shown, a practitioner may decrease a diameter of an opening of the torque device 150 through which the guidewire 102 is placed. When the diameter of the opening is equivalent to the diameter of the guidewire 102, the torque device 150 physically engages with the guidewire 102 such that the position of the torque device 150 relative to the guidewire 102 is fixed. Components configured for gripping or securing the guidewire 102 are discussed in more detail below.

The torque device 150 may permit the practitioner to have enhanced or greater rotational control and axial displacement control of the guidewire 102. For instance, the torque device 150 has a greater diameter than the guidewire 102, thereby providing a larger surface to grip while the practitioner is manipulating the guidewire 102. Also, when the torque device 150 is secured to the guidewire 102, the coupling of the torque device 150 and the hemostasis valve 110 may prevent axial displacement.

The torque device 150 may comprise a handle 158, a torque nut 152, and a collet (not shown in FIG. 1). The collet may be a collar with a segmented portion. A diameter of the segmented portion may be adjusted by applying or removing a compressing force. The handle 158 and the torque nut 152 may provide the compressing force. For example, when the handle 158 is axially displaced relative to the torque nut 152, the compressing force may be altered. In some embodiments, the axial displacement may be controlled via a threaded interface between the handle 158 and the torque nut 152. In some embodiments, a set of gripping elements 154 may assist in rotating the torque nut 152. In some embodiments, the interface may facilitate a direct push or pull of the handle 158 in the axial direction to alter the compression force. In some embodiments, the compressing force may be automatically controlled via an actuator.

The hemostasis valve 110 is configured to prevent fluid loss while allowing medical devices to enter a valve lumen. The hemostasis valve 110 may include an intravascular access connector 120, a body 130, and a compression nut 140.

The intravascular access connector 120 may be located at a distal end of the body 130. The intravascular access connector 120 may couple to various medical devices such as a catheter 104 or an introducer. The intravascular access connector 120 may include a second set of gripping elements 124 to assist in attaching the intravascular access connector 120 to a medical device.

The body 130 may include a valve lumen to provide a passage from a distal end to a proximal end. Medical devices, tissue samples, or fluids may be distributed through the valve lumen. A seal within the compression nut 140 may provide a hemostatic entrance to the valve lumen. A sidearm 132 may be coupled to the body 130 and provide a secondary access passage to the valve lumen.

The hemostasis torque assembly 100 may comprise a seal actuator, configured to selectively seal the valve lumen. The seal actuator may be configured to alter the diameter of a sealable opening in the seal, allowing a practitioner to obstruct fluid passage through the valve lumen. The seal actuator may facilitate sealing of the valve lumen around an elongate instrument such as a guidewire. In the illustrated embodiment, the compression nut 140 is an exemplary embodiment of a seal actuator. In the illustrated embodiment, a practitioner may use the compression nut 140 to adjust a seal. For example, the diameter of an opening in the seal may change based on a rotational movement of the compression nut 140. The compression nut 140 may include a third set of gripping elements 144 to assist in rotating the compression nut 140. The gripping elements (124, 144, 154) in the illustrated embodiment include a plurality of ridges. However, the gripping elements may comprise other structures, such as divots, high-friction surfaces, and/or slots.

The hemostasis valve 110 and the torque device 150 may selectively couple in various ways. In some embodiments, the mating interface may include threading, spring-loaded pins, or other coupling means. In one embodiment, a snap-fit mating interface may couple the hemostasis valve 110 and the torque device 150. A snap-fit mating interface may comprise a ridge on one of the components and a catch on the other component that retains the ridge. An axial force may couple and uncouple the snap-fit mating interface. Further, the snap-fit mating interface may allow the hemostasis valve 110 and the torque device 150 to rotate relative to each other.

In some embodiments, the snap-fit mating interface may provide resistance to maintain a rotational position. The resistance may prevent unintentional rotational movement of an inserted guidewire. In some embodiments, the torque nut 152 may comprise indicators 174 and the compression nut 140 may comprise indicators 175 that indicate the rotational position of the torque device 150 relative to the hemostasis valve 110.

The coupling of the hemostasis valve 110 and the torque device 150 may also fix the axial movement of the guidewire 102 secured by the torque device 150. For instance, the coupling prevents a physician from inserting the guidewire 102 further without manipulating the torque device 150 to release the guidewire 102. Further, the coupling causes a physician to apply an additional amount of force to remove the guidewire 102 than if the guidewire 102 was not retained by the torque device 150.

Figure 2:
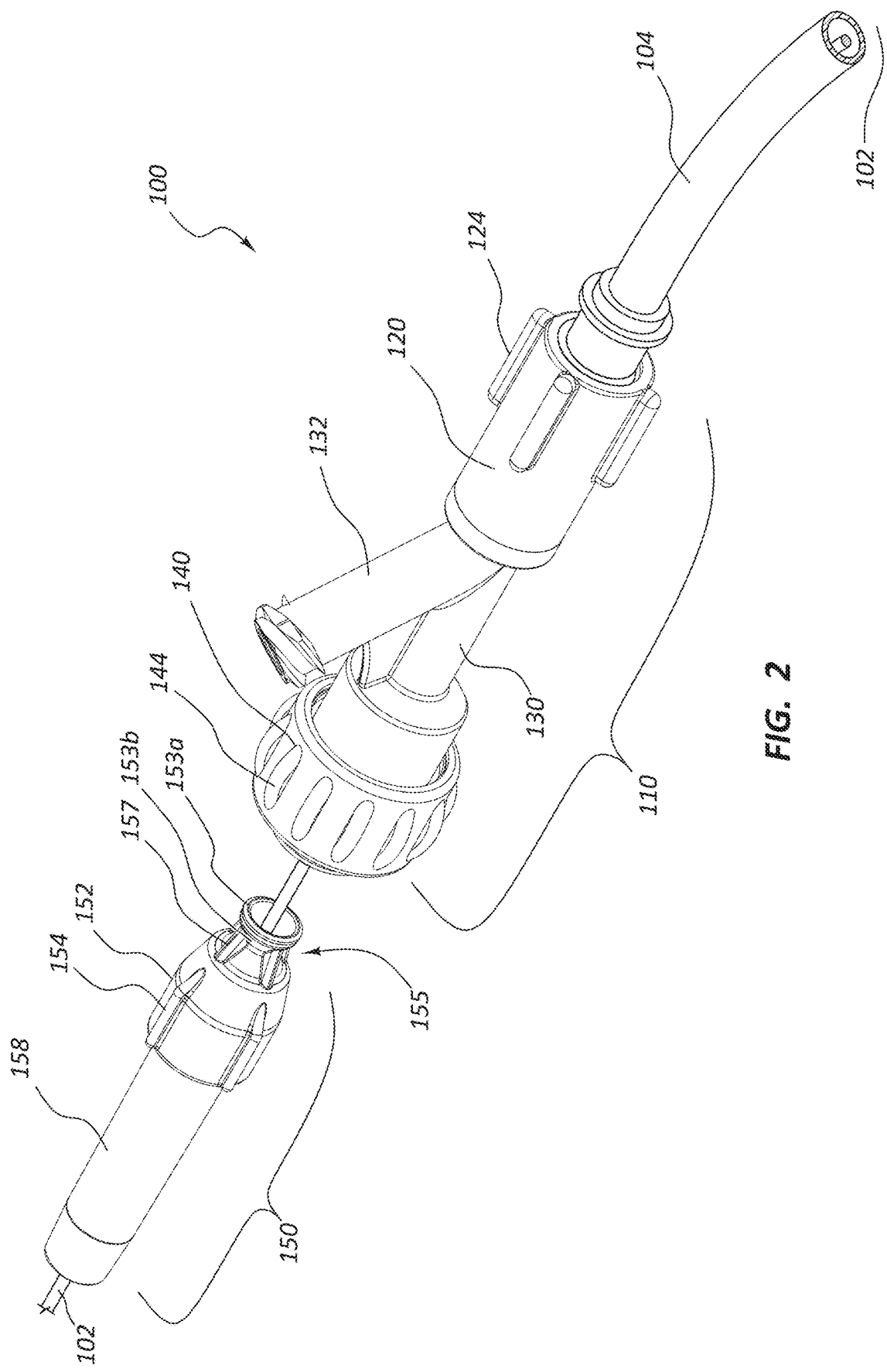
FIG. 2 illustrates a perspective view of the hemostasis torque assembly illustrated in FIG. 1 in an uncoupled position, according to one embodiment.

FIG. 2 illustrates a perspective view of the hemostasis torque assembly 100 illustrated in FIG. 1 in an uncoupled position, according to one embodiment. In the illustrated embodiment, a tip 155 is configured to slide within the compression nut 140. The tip 155 may have a conical shape to assist a practitioner inserting the torque nut 152.

As shown, the torque nut 152 may comprise the tip 155 with a ridge 153a. The ridge 153a may be formed from a flare 153b at a distal end of the tip 155. The flare 153b may be supported by a plurality of braces 157. The ridge 153a may be configured to catch within a groove 143a (FIG. 4A) in the compression nut 140 to couple the torque device 150 to the hemostasis valve 110.

The torque device 150 and the hemostasis valve 110 may selectively change between a coupled and an uncoupled position. For example, a practitioner may couple the torque device 150 to the hemostasis valve 110 and insert the guidewire 102. When a target location is reached, the physician may use the torque device 150 to secure the position of the guidewire 102. The practitioner may rotate the torque device 150 to alter the rotational position of the guidewire 102. However, the coupling maintains the axial position of the secured guidewire 102. To alter the axial position, a physician may unsecure the guidewire 102 or provide an axial force to decouple the torque device 150 from the hemostasis valve 110.

Figure 3:
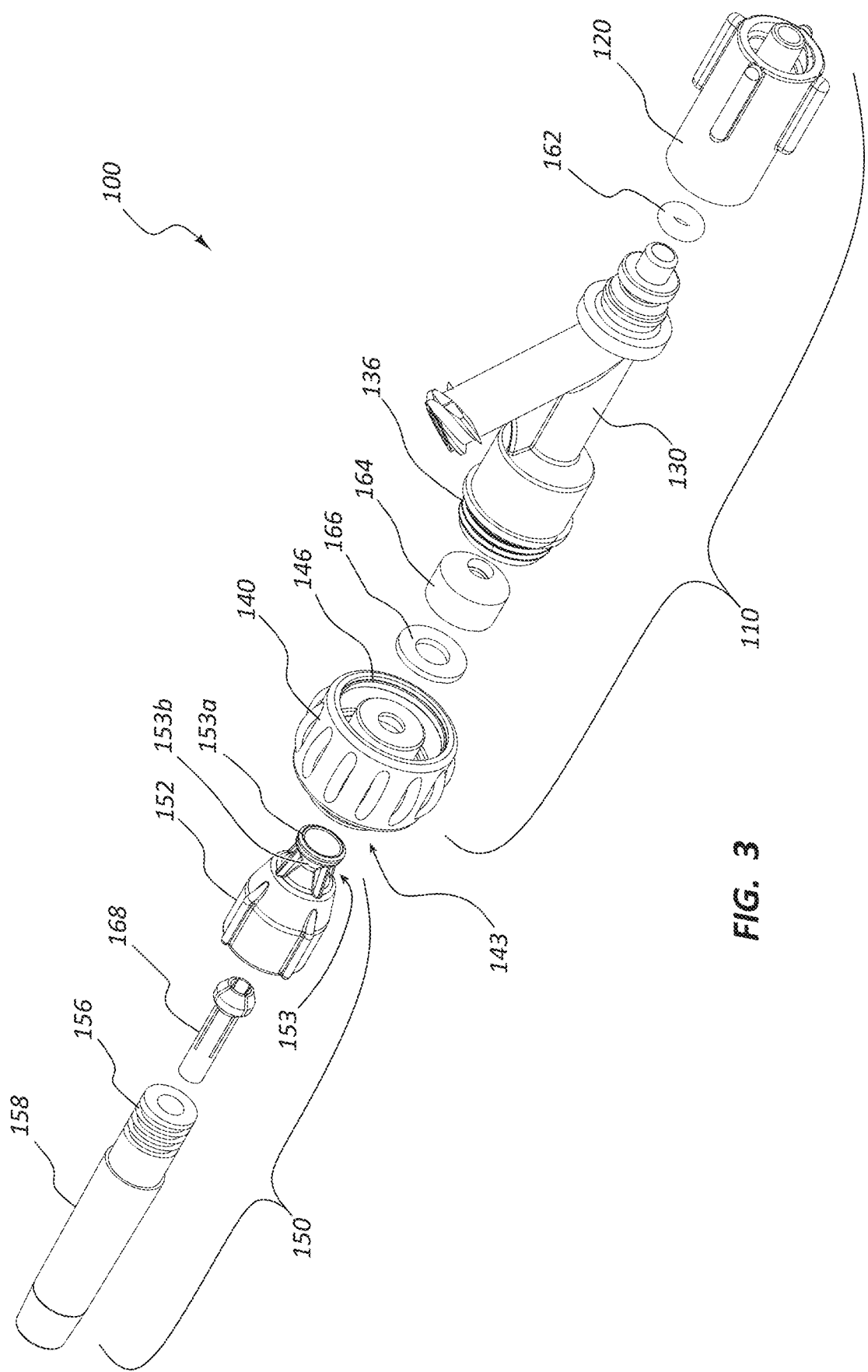
FIG. 3 illustrates an exploded view of the hemostasis torque assembly illustrated in FIG. 1, according to one embodiment.

FIG. 3 illustrates an exploded view of the hemostasis torque assembly 100 illustrated in FIG. 1. This exploded view is one example of components that may be used to assemble the hemostasis torque assembly 100. The hemostasis torque assembly 100 may include the hemostasis valve 110 and the torque device 150. The hemostasis valve 110 and the torque device 150 may selectively couple. For example, the hemostasis valve 110 may include a first mating interface 143 such as the groove 143a (FIG. 4A), and the torque device 150 may include a second mating interface 153 such as the ridge 153a. A practitioner may apply an axial force to couple and uncouple the torque device 150 from the hemostasis valve 110.

The torque device 150 may include the handle 158, the torque nut 152, and a collet 168. The handle 158 may couple to the torque nut 152 via a threaded interface 156. The collet 168 may be partially disposed within both the handle 158 and the torque nut 152. For example, a distal end of the collet 168 may be housed within the torque nut 152, and a proximal end of the collet 168 may be housed within the handle 158. The collet 168 may also have a bulbous distal end that does not fit within the lumen of the handle 158. Because the collet 168 does not entirely fit within the handle 158, the handle 158 forces the bulbous distal end further into the torque nut 152 when the handle 158 transitions toward the torque nut 152.

The hemostasis valve 110 may comprise the intravascular access connector 120, the body 130, the compression nut 140, and a seal 164. The intravascular access connector 120 may be coupled to a distal end of the body 130. A gasket 162 may seal the coupling. The seal 164 may be housed within a distal end of the body 130.

A threaded interface 136 on a proximal end of the body 130 may mate with a threaded interface 146 on the compression nut 140. As the compression nut 140 is rotated onto the threaded interface 136 of the body 130, the axial position of the compression nut 140 may move toward the body 130. A washer 166 may form a contact between the compression nut 140 and the seal 164. The seal 164 may be made of an adaptable material that flexes and changes shape based on a pressure applied by the compression nut 140. For example, the seal 164 may include an aperture that alters diameter as the compression nut 140 moves toward and away from the body 130.

FIGS. 4A and 4B illustrate the effects of an adjustment to the threaded interface 146 of the hemostasis valve 110 and an adjustment to the threaded interface 156 of the torque device 150.

FIG. 4A illustrates a cross-sectional view of the hemostasis torque assembly 100 of FIG. 1 taken through plane 4A-4A in a first position where the guidewire 102 is unsecured and may be manipulated in an axial or rotational direction. The torque device 150 and the hemostasis valve 110 may be coupled via a mating junction 173 described in further detail with reference to FIG. 5.

As shown, a diameter of a lumen within the collet 168 may be large enough to allow the guidewire 102 to pass through. In this first position, a practitioner may push or pull the guidewire 102 freely to adjust its longitudinal position. For example, when a practitioner places the guidewire 102 in a patient, the practitioner may advance the guidewire 102 to a treatment site while the hemostasis torque assembly 100 is in this first position. Further, in this first position, the aperture of the seal 164 is large enough to allow fluid passage. To form a hemostatic seal, the compression nut 140 may be threaded further onto the body 130 as shown in FIG. 4B.

FIG. 4B illustrates a cross-sectional view analogous to the view of FIG. 4A of the hemostasis torque assembly 100 of FIG. 1 in a second position where the guidewire 102 is secured by the torque device 150. As shown, both the aperture of the seal 164 and the diameter at the end of the lumen of the collet 168 may be altered. The seal 164 and the collet 168 may be adjusted independently. For example, the aperture of the seal 164 may be closed around the guidewire 102 to form a hemostatic seal while the collet 168 may remain in the position as shown in FIG. 4A to allow a practitioner to advance the guidewire 102 further into a patient.

As shown, both the collet 168 and the seal 164 may feature chamfered surfaces. As the threaded interfaces 146 and 156 are tightened, the handle 158 and the compression nut 140 place an axial force on the collet 168 and the seal 164 respectively. The chamfered surfaces of the collet 168 and the seal 164 may be forced along sloped surfaces of the torque nut 152 and the body 130, causing the openings of both the seal 164 and the collet 168 to close.

Figure 5:
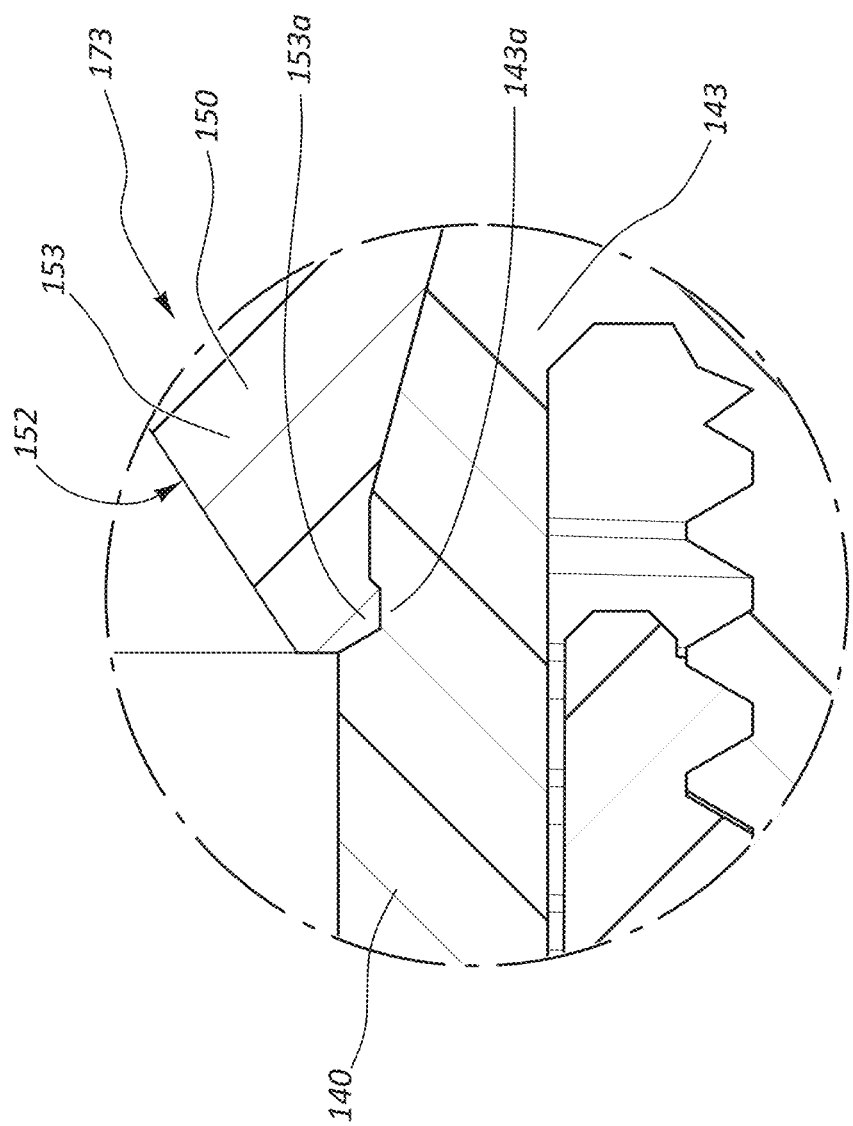
FIG. 5 illustrates a detail view, taken around line 5, of a mating junction of the hemostasis torque assembly of FIG. 4A, according to one embodiment.

FIG. 5 illustrates a detail view, taken around line 5, of the mating junction 173 of the hemostasis torque assembly 100 of FIG. 4A. The mating junction 173 may include a first mating interface 143 within the compression nut 140, and a second mating interface 153 (e.g., the ridge 153a) on an exterior surface of the tip 155 of the torque nut 152. As shown, in some embodiments, the first mating interface 143 may be the groove 143a, and the second mating interface 153 may be the ridge 153a.

The first mating interface 143 and the second mating interface 153 (e.g., the ridge 153a) may selectively couple via an axial force. For example, a practitioner may push the compression nut 140 and the torque nut 152 together. As the practitioner pushes, the tip 155 of the torque nut 152 may flex as it travels along an inner surface of the compression nut 140. Then when the second mating interface 153 (e.g., the ridge 153a) reaches the first mating interface 143, the tip 155 of the torque nut 152 may spring back from the flexed state and cause the second mating interface 153 to pair with the first mating interface 143. If a practitioner were to apply a pulling force to the hemostasis torque assembly 100 in a coupled position, the flex of the tip 155 of the torque nut 152 may facilitate removal of the torque nut 152 from the compression nut 140.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub-routines or only a portion of a method described herein may be a separate method within the scope of this disclosure. Stated otherwise, some methods may include only a portion of the steps described in a more detailed method.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated by one of skill in the art with the benefit of this disclosure that in the above description of embodiments, various features are sometimes grouped together in a single embodiment, figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. It will be apparent to those having skill in the art that changes may be made to the details of the above-described embodiments without departing from the underlying principles of the present disclosure.

The invention claimed is:

1. A hemostasis torque assembly comprising:
a body comprising a valve lumen extending from a proximal end to a distal end of the body;
a seal in communication with the valve lumen, the seal comprising a sealable opening;
a seal actuator configured to selectively alter a diameter of the sealable opening;
a first mating mechanism adjacent the proximal end of the body;
a torque element comprising a second mating mechanism configured to selectively couple to the first mating mechanism such that the torque element is configured to selectively couple to and decouple from the body; and
a collet handle,
wherein the torque element is configured to provide a force to maintain a position of a guidewire coupled to the torque element;
wherein the seal actuator comprises a compression nut;
wherein the torque element comprises a torque nut and a collet; and
wherein an axial position of the collet handle relative to the torque nut alters a clamping force of the collet.

2. The hemostasis torque assembly of claim 1, wherein the body further comprises a sidearm, the sidearm comprising a sidearm lumen extending therethrough, the sidearm lumen in fluid communication with the valve lumen.

3. The hemostasis torque assembly of claim 1, wherein the first mating mechanism comprises a groove, and the second mating mechanism comprises a ridge on an exterior surface of the torque element.

4. The hemostasis torque assembly of claim 1, wherein the first mating mechanism is disposed on the seal actuator.

5. The hemostasis torque assembly of claim 1, wherein the first mating mechanism comprises a groove, and the second mating mechanism comprises a flare at a distal end of the torque element.

6. The hemostasis torque assembly of claim 1, wherein the torque nut and the compression nut are rotatable relative to each other, and each comprises rotational indicators.

7. The hemostasis torque assembly of claim 1, wherein the torque nut and the compression nut are rotatable relative to each other, and the first and the second mating mechanisms comprise indexing to provide tactile feedback to a user when the torque nut is rotated.

8. The hemostasis torque assembly of claim 1, wherein the first and second mating mechanisms are coupled via an axial force.

9. The hemostasis torque assembly of claim 1, wherein the torque nut comprises a tip that tapers for a portion and flares at a distal end of the tip, and wherein an aperture of the compression nut conically narrows and comprises a groove to retain the flared distal end of the tip.

10. A hemostatic torqueing system to fix a position of a guidewire with respect to a hemostasis valve, the system comprising:
- a hemostasis valve to minimize fluid loss while permitting introduction of a guidewire;
- a torque device to apply a clamping force to the guidewire; and
- a mating junction to selectively couple the hemostasis valve to the torque device, the mating junction comprising:
  - a first mating interface within a proximal portion of the hemostasis valve, and
  - a second mating interface on an exterior surface of a distal portion of the torque device,
  - wherein the hemostasis valve and the torque device selectively couple and decouple via an axial force.

11. The hemostatic torqueing system of claim 10, wherein the torque device provides the clamping force in response to a rotational force applied to the torque device by a user.

12. The hemostatic torqueing system of claim 10, wherein the hemostasis valve seals an opening in response to a rotational force applied to the hemostasis valve by a user.

13. The hemostatic torqueing system of claim 11, wherein the first mating interface and the second mating interface, when coupled together, provide rotational resistance such that a rotational force applied to one of the torque device and the hemostasis valve rotates both.

14. The hemostatic torqueing system of claim 11, wherein the torque device and the hemostasis valve comprise gripping elements that allow a rotational force to be applied individually to the torque device and the hemostasis valve.

15. The hemostatic torqueing system of claim 10, wherein the first mating interface comprises a groove, and the second mating interface comprises a ridge.

16. The hemostatic torqueing system of claim 10, wherein the torque device is rotatable relative to the hemostasis valve, and the torque device comprises rotational indicators designating rotational displacement.

17. The hemostatic torqueing system of claim 16, wherein the torque device is rotatable relative to the hemostasis valve, and the mating junction further comprises indexing to provide tactile feedback to a user when the torque device is rotated.

* * * * *